United States Patent [19]

Leon et al.

[11] Patent Number: 5,476,524
[45] Date of Patent: Dec. 19, 1995

[54] OIL PRODUCING SUNFLOWERS AND PRODUCTION THEREOF

[75] Inventors: Alberto J. Leon, Ames, Iowa; Simon T. Berry, Reading, United Kingdom; George K. Rufener, II, Johnston; Ronald P. Mowers, Ames, both of Iowa

[73] Assignee: Zeneca Limited, London, England

[21] Appl. No.: 165,303

[22] Filed: Dec. 9, 1993

[51] Int. Cl.$^6$ .............................. A01H 1/02; A01H 1/04; C12N 15/29

[52] U.S. Cl. .................................. 47/58; 435/6; 800/200; 800/DIG. 14

[58] Field of Search .................... 47/58, 58.03; 435/6; 800/200, DIG. 14

[56] References Cited

PUBLICATIONS

Areco, C. M., D. Alvarez. and A. Ljubich. 1985. Diallelic analysis of grain yield and oil content in six sunflower cultivars. pp. 755–759. In Proc. 11th Sunflower International Conference. Mar del Plata, Buenos Aires, Argentina. 10–13 Mar. Asoc. Argentina de Girasol, Bs. As.
Bedov, S. 1985. A study of combining ability for oil and protein contents in seed of different sunflower inbreds. pp. 675–682. In Proc. 11th Sunflower International Conference. Mar del Plata, Buenos Aires, Argentina. 10–13 Mar. Asoc. Argentina de Girasol, Bs. As.
Choumane, W., and P. Heizmann. 1988. Structure and variability of nuclear ribosomal genes in the genus *Helianthus*. Theor. Appl. Genet. 76:481–489.
Dedio, W. 1982. Variability in hull content, kernel oil content, and whole seed oil content of sunflower hybrids and parental lines. Can. J. Plant. Sco. 62:51–54.
Diers, B. W., P. Keim, W. R. Fehr, and R. C. Shoemaker. 1992. RFLP analysis of soybean seed protein and oil ocntent. Theor. Appl. Genet. 83:608–612.
Edwards, M. D., C. W. Stuber, and J. F. Wendel. 1987. Molecular–marker facilitated investigations of quantitative–trait loci in Maize. I. Numbers, genomic distribution and types of gene action. Genetics 116:113–125.
Edwards, M. D., T. Helentjaris, S. Wright, and C. W. Stuber. 1992. Molecular–marker–facilitated investigations of quantitative trait loci in maize. Theor. Appl. Genet. 83:765–774.
Fick, G. N. 1975. Heritability of oil content in sunflower. Crop Sci. 15:77–78.
Gentzbittel L., A. Perrault, P. Nicolas. 1992. Molecular phylogeny of the *Helianthus* genus, based on nuclear restriction fragment length polymorphism (RFLP). Mol. Biol. Evol. 9:872–892.
Gupta, K. K., and K. R. Khanna. 1982. Gene action and heterosis for oil yield and component characters in sunflower. Indian J. Genet. 42:265–271.
Krauter, R., A. Steinmetz, and W. Friedt. 1991. Efficient interspecific hybridization in the genus *Helianthus* vis "embryo rescue" and characterization of the hybrids. Theor. Appl. Genet. 82:521–525.
Leclercq, P. 1966. Une sterile male utilisable pour la production d'hybrides simples de tournesol. Ann. Ameloir. Plantes (Paris) 16:134–144.
Leclercq, P. 1979. Heredite du caractere "Grain blanc" chez le tournesol (*Helianthus annuus*). Ann. Ameloir. Plantes (Paris) 26(6):107–109.
Martinez, F. J., F. Marquez, and J. Ortiz Ortiz. 1979. Genetic (List continued on next page.)

*Primary Examiner*—David T. Fox
*Attorney, Agent, or Firm*—Dana Rewoldt

[57] ABSTRACT

Sunflower seed color is determined by pigmentation of three layers of the sunflower pericarp (hull), epidermis, hypodermis, and phytomelanin layer. The present invention identifies RFLP markers linked to factor(s) affecting seed hypodermis pigmentation and identifies the relation between this trait and oil percentage in the sunflower seed. Seeds with white hypodermis had lower oil percentage than those with unpigmented hypodermis. The Hyp factor was found located in the same map interval region as one QTL with major effects on seed oil percentage. The linkage between the top factor and the QTL with the seed oil can be employed in breeding sunflowers to improve seed oil percentage.

3 Claims, 8 Drawing Sheets

```
C    C         C    C         C         C         C
0    0    H    0    1         1         0         1
3    2    Y    8    7         0         6         2
5    9    P    8    2         0         6         0
7    0         7    0         2         7         7
├────┼────┼────┼────┼─────────┼─────────┼──────⌇⌇──┤
  10   7   16   15      23        23        37
```

OTHER PUBLICATIONS of oil content in sunflower seed. (In Spanish). In Ann. I.N.I.A. Serv. Prod. Veg 10:93–99. Andalucia, Spain.

Miller, J. F., G. N. Fick, and W. W. Roath. 1982. Relationships among traits of inbreds and hybrids of Sunflower. pp. 238–240. In Proc. 10th International Sunflower Conference. Surfers Paradise, Australia. 14–18 Mar. Int. Sunflower Assoc.

Mosjidis, J. A. 1982. Inheritance of color in the pericarp and corolla of the disc florets in sunflower. The J. of Heredity 73:461–464.

Paterson, A. H., E. S. Lander, J. D. Hewitt, S. Peterson, S. E. Lindoln, and S. D. Tanksley. 1988. Resolution of quantitative traits into Mendelian factors by using a complete linkage map of restriction fragment length polymorphisms. Nature 335:721–726.

Pawlowski, S. H. 1964. Seed genotype and oil percentage relationships between seeds of a sunflower. Can. J. Genet. Cytol. 6:293–297.

Putt, E. D. 1940. Observation on morphological characters and flowering processes in the sunflower (*Helianthus annuus* L.). Sci. Agr. 21:167–179.

Putt, E. D. 1944. Histological observations on the location of pigments in the akene wall of the sunflower (*Helianthus annuus* L.). Sci. Agr. 25:185–188.

Refoyo, A., L. M. Martin, and J. M. Serradilla. 1986. Inheritance of oil content in sunflower achenes and almonds. (In Spanish.) pp. 436–441, In Proc. 12th International Sunflower Conference. Novi. Sad, Yugoslovia. 25–29 Jul. Yugoslav Assoc of Producers of Plant Oil and Fat.

Russell, W. A. 1953. A study of the inter–relationships of seed yield, oil content, and other agronomic characters with sunflower inbred lines and their top crosses. Can J. Agr. Sci. 33:291–314.

Thompson, T. E., G. N. Fick, and J. R. Cedeno. 1979. Maternal control of seed oil percentage in sunflower. Crop. Sci. 19:617–619.

Lander, E. S., David Botstein. 1989. Mapping Mendelian Factors Underlying Quantitative Traits Using RFLP Linkage Maps. Genetics Society of America. pp. 185–199.

SCALE: 5cM

OIL PRODUCING SUNFLOWERS AND PRODUCTION THEREOF

BACKGROUND OF THE INVENTION

Most cultivated sunflower is grown as a source of vegetable oil. Thus, one of the principal goals of sunflower breeding programs is the development of F1 hybrid cultivars with high oil yield. Sunflower oil yield per unit area is determined by the product of seed yield per unit area and oil percentage in the seed. Therefore, consideration of both components is important when breeding for high oil yield hybrids.

Increased seed oil percentage is an important objective when breeding for high oil yield in sunflower. Although some researchers have investigated the genetics and heritability of sunflower oil percentage, most analyses were conducted on the oil percentage in the whole seed through conventional breeding and biometric procedures. This invention identifies restriction fragment length polymorphisms (RFLPs) linked to quantitative trait loci (QTL) affecting seed oil percentage, kernel oil percentage and kernel percentage. The advent of restriction fragment length polymorphisms (RFLPs) as genetic markers has enabled the development of linkage maps.

The number of factors controlling seed oil percentage or its components has not been discovered nor has their use in production of a genetically desirable inbred been suggested. However, some research has been done to study gene action involved in the expression of the traits. Additive, dominant, and epistatic effects were determined for seed oil percentage using two $F_2$ populations and their reciprocal backcrosses. Estimates of General (GCA) and Specific Combining Ability (SCA) indicated additive effects were more important for seed oil percentage. Significant additive effects were also reported for seed oil, kernel oil, and kernel percentages, although significant dominant effects for seed oil percentage and kernel percentage were detected in irrigated conditions. Additive gene action has also been reported for hull percentage. Dominant and complementary effects for seed oil percentage and dominant effects for kernel oil percentage have been suggested. In general, these results indicate that additive effects predominantly influence oil percentage in the whole seed and its components; however, some non-additive effects also seem to affect these traits.

The difficulty in understanding the genetic basis of some traits may be due to the lack of knowledge about gene number, location, gene action and effects. This situation has focused the attention on the use of molecular markers to detect linkage with quantitative trait loci (QTL).

Cultivated sunflower is a diploid species ($2n=2x=34$) and is second only to soybean in its importance as an annual oilseed crop. However the genetics of only a small number of traits have been studied in detail as a consequence of this sunflower does not possess a classical genetic map. The only linkage reported to date is that between the nuclear genetic male sterility (GMS) gene and the T gene coding for anthocyanin pigmentation in the plant (Leclerq P (1966) Ann Amerlior Plantes 16:135–144). In addition the use of molecular markers in sunflower has only focused on the identification of interspecific crosses (Krauter R, et al (1991) Theor Appl Genet 82:521–525) and the taxonomy of the genus Helianthus (Choumane W, et al. (1988) Theor Appl Genet 76:481–489). A recent fingerprinting study of elite inbred lines has shown that there are high levels of restriction fragment length polymorphism in cultivated sunflower. Since sunflower is a diploid with developed inbred lines and segregating populations there remains a need to RFLP map the sunflower.

SUMMARY OF THE INVENTION

An object of the present invention is to provide an RFLP map which can be employed to assist in breeding sunflowers and identify and locate the chromosomal regions associated with selected traits.

Still another object of the present invention is identify and introgress high oil chromosomal regions into sunflower lines.

A further object of the present invention is to provide an improved method of breeding high yielding, high oil sunflowers by employing a visual screening of seed color.

An additional object of the present invention is to provide an improved method of breeding for a selected trait by employing RFLP data.

The present invention encompasses sunflower breeding methods employing a sunflower RFLP map for producing progeny sunflowers having improved seed oil content from a first parent line having high yield traits and low seed oil traits and a second parent line having a higher seed oil trait, then said first parent line said method comprising the steps of: crossing said first parent line with said second parent line to form a plant population; gathering RFLP data on said plant population and selecting plants from said population which have linkage blocks which indicate the higher seed oil trait of the second parent; breeding said selected plants wherein a high seed oil content trait is evidenced in said progeny.

A method of identifying chromosomal regions of the sunflower associated with selected traits comprising the steps of: employing RFLP probes to locate chromosomal regions of the sunflower; mapping said RFLP probes on a RFLP map whereby selected traits can be identified and located. A method of breeding for sunflower progeny having improved seed oil traits beyond the seed oil trait evidenced by at least one parent comprising the steps of: crossing a first sunflower having a first seed color associated with high seed oil trait with a second sunflower having a second seed color to form a plant population;selecting plants having first said seed color from said plant population whereby further breeding of said selected plants produces progeny characterized by said first seed color and said high oil trait.

DETAILED DESCRIPTION OF THE INVENTION

Figure 1A:
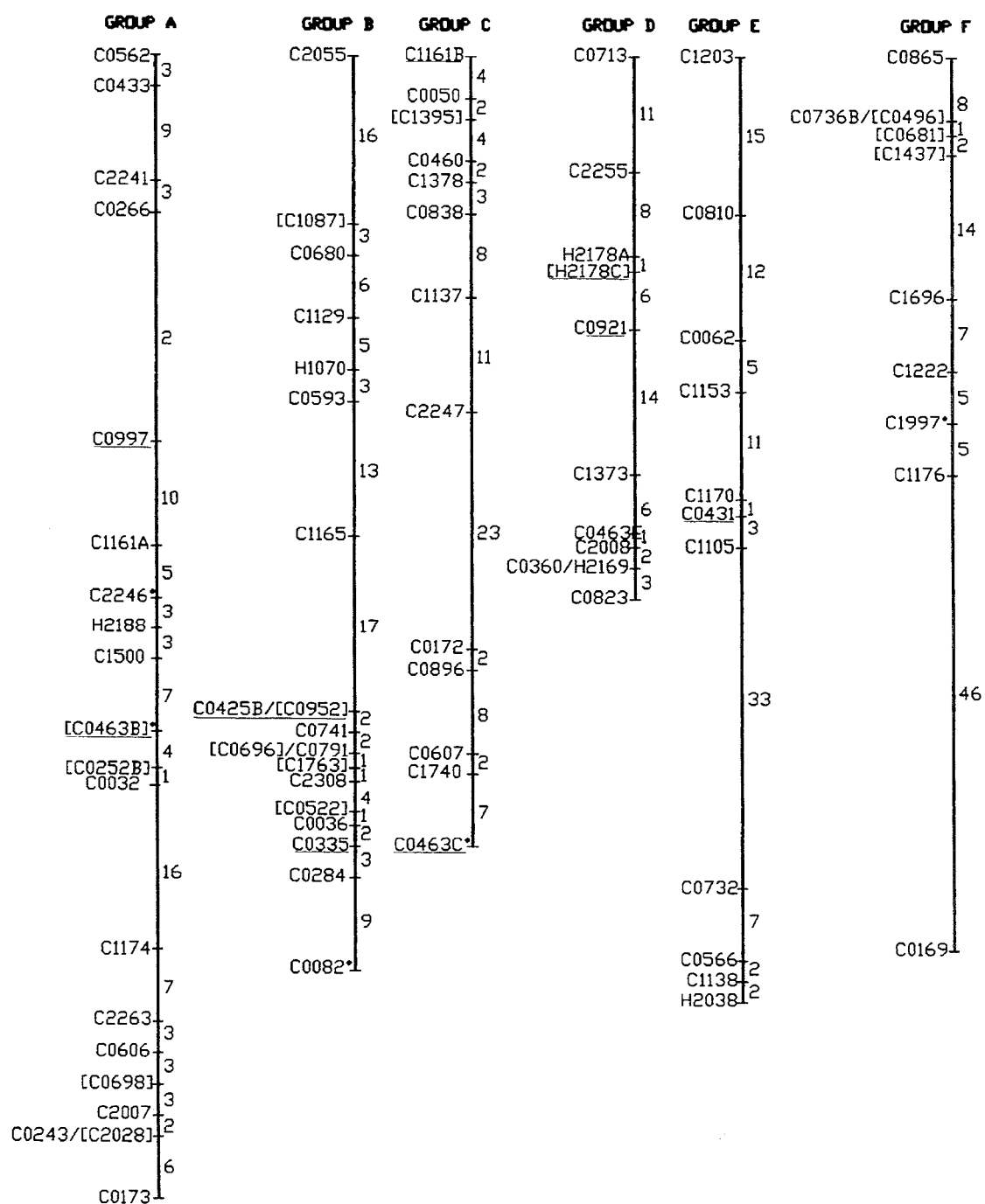
FIGS. 1A, 1B, 1C Sunflower RFLP linkage map of 234 loci identified by 213 probes. The seventeen linkage groups are listed at the top, the loci listed on the right and the map distances in centiMorgans (cM) on the left. The nomenclature of the RFLP loci is described in "Materials and Methods". Loci mapped as dominant markers are underlined and those deviating from the expected Mendelian segregation ratios (P<0.05) are indicated with *. The loci with uncertain map positions are indicated by the square brackets.

Broadly the invention was developed in a three step process. The first step was development of the chromosomal RFLP map; the second step was the identification of the chromosomal linkage blocks associated with the high oil trait; the third step was developing a breeding method that could employ a visual screening for the high oil trait or a RFLP screening for the high oil trait due to the seed color traits identified and associated with the same chromosomal region that carries the high oil trait.

A detailed linkage map of *Helianthus annuus* was constructed based on the segregation of 234 RFLP loci, detected by 213 probes, in an $F_2$ population of 289 individuals (derived from a cross between the inbred lines HA89 a public line that is high oil and low yield and ZENB8 an inbred line that is lower oil and high yield). The genetic markers covered 1380 centiMorgans (cM) of the sunflower genome and were arranged in 17 linkage groups, corresponding to the haploid number of chromosomes in this species. One locus was found to be unlinked. Although the average interval size was 5.9 cM, there were a number of regions larger than 20 cM that were devoid of markers. Genotypic classes at twenty-three loci deviated significantly from the expected ratios (1:2:1 or 3:1) all showing a reduction in the ZENB8 homozygous class. The majority of these loci were found to map to four regions on linkage groups G, L and P.

The present invention includes a RFLP map for sunflowers which identifies QTL affecting seed oil content and other agronomic traits.

Materials and methods

The general molecular biology methods followed are those described by Sambrook J, et al. (1989) Molecular cloning. A laboratory manual, 2nd edn Cold Spring Harbour Laboratory Press, Cold Spring Harhbour, N.Y.

Plant material

An F2 population (289 individuals) was made by selfing a single $F_1$ of the proprietary inbred line ZENB8 crossed to the public line HA89 (USDA). The $F_2$ population thus produced was also segregating for traits such as seed color, seed oil content, seed length, days to flowering and head and stem diameter.

RFLP probes

In total 361 cDNAs isolated from etiolated seedlings (coded with the prefix C) and 29 PstI genomic clones (coded with the prefix H) had been selected as low copy RFLP probes from the libraries of Zeneca Seeds, U.K. These were screened against the two parental lines digested with one of five restriction enzymes (DraI, EcoRI, EcoRV, HindIII and XbaI) to identify the polymorphic markers. Twenty-four of the RFLP probes mapped were obtained through GIE Cartisol, France.

DNA isolation, digestion and Southern blotting

Three fully expanded leaves were cut from each $F_2$ plant and frozen on dry ice for transportation to the laboratory. The leaf tissue was then lyophilized, ground to a fine powder in a mill and DNA extracted using a modified version of the protocol described by Rogers SO, et al. (1985) Pl Mol Biol 5:69–76. The DNA was quantified fluorimetrically and digested to completion using 4 units of enzyme/microgramme according to the manufacturers instructions (Northumbria Biologicals Ltd.). Ten microgrammes of DNA/lane were loaded onto 1.0% TBE-agarose (Seakern) slab gels and electrophoresis performed overnight at 3 Volts/cm. The DNA was transferred onto Hybond-N membrane (Amersham) via Southern blotting with 20×SSC and fixed by baking for 2 hours at 80° C., followed by UV cross-linking at 60 mJ in a Stratalinker (Stratagene).

Hybridizations

Probe fragments were generated from recombinant plasmids using PCR and the products gel-purified prior to labelling with [$\alpha$-$^{32}$P] dCTP (Amersham) via random priming (Feinberg and Vogelstein 1983). The unincorporated radioactivity was removed by spin-column chromatography using Sephadex G50 (Sigma). Hybridizations were performed at 60° C. overnight using standard conditions and the excess probe removed by two, 30 minute washes in 0.5× SSC, 0.1% SDS at 60° C. Filters were exposed to XOMAT-AR X-ray film (Kodak) with two intensifying screens at −80° C. After autoradiography the radioactive probes were removed from the filters by two 20 minute washes in 0.1×SSC, 0.5% SDS at 80° C.

Linkage analysis

Autoradiographs were independently scored twice and if conflicts in scoring arose and could not be resolved, the data were excluded from the analysis. If more than 5% of the RFLP scores for a given locus were missing, the hybridization was repeated. The segregation of the alleles at each locus was checked against the expected ratios for codominant (1:2:1) and dominant (3:1) markers using the Chi-squared test, with a significance level of 5%.

The genetic map was constructed using the MAPMAKER computer program version 3.0 (Lander ES, et al. (1987) MAPMAKER: An interactive computer package for constructing primary genetic linkage maps of experimental and natural populations. Genomics 1:174–181). Initially a two point linkage analysis was conducted to determine the maximum likelihood recombination fraction and the LOD score for each of the possible pairs of loci. Linkage groups were formed using the "group" command on the two point data with recombination values less than 0.35 and a constant LOD score of 3.0.

Three point linkage analyses were conducted for the loci within each group and these data used in conjunction with the "order" command. The "order" function tries to find a subset of five informative loci to start building the linkage group; however this starting point is random and different orderings of loci can be found for the same group. Therefore the "order" function was repeated several times for each group to try and find the one containing the largest number of loci. These orders were then tested using the multipoint function "ripple" and the loci whose positions were ambiguous (i.e. those placed automatically at a LOD of 2.0) were noted.

Loci which had been excluded on the basis of the three point linkage data were placed using the "try" command and initially unlinked loci were mapped using the "near" command by increasing the recombination default to 0.50. The Kosambi function was used to obtain the centiMorgan (cM) values (Kosambi 1944).

Multiple loci detected by a single probe were coded with the probe number plus the suffix A, B, C or D etc. to indicate each duplicate locus.

Probe selection and segregation

From the three hundred and ninety RFLP clones screened against the parental inbred lines, two hundred and thirteen (55%) detected polymorphism. The majority of these were revealed in digestions with the restriction enzymes EcoRI or EcoRV (Table 1).

TABLE 1

The numbers of probes mapped in conjunction with the five restriction enzymes used to reveal polymorphism between the parental inbreds HA89 and ZENB8.

| Enzyme | EcoRV | EcoRI | HindIII | DraI | XbaI | Total |
|---|---|---|---|---|---|---|
| No. of probes | 92 | 89 | 22 | 8 | 2 | 213 |

In general, probe/enzyme combinations were chosen on the basis of their ability to reveal clear and simple polymorphism in order to make the interpretation of the RFLP data more reliable. In total the 213 polymorphic probes detected 235 loci, with only 25 of these scored as dominant markers (3:1).

Figure 1B:
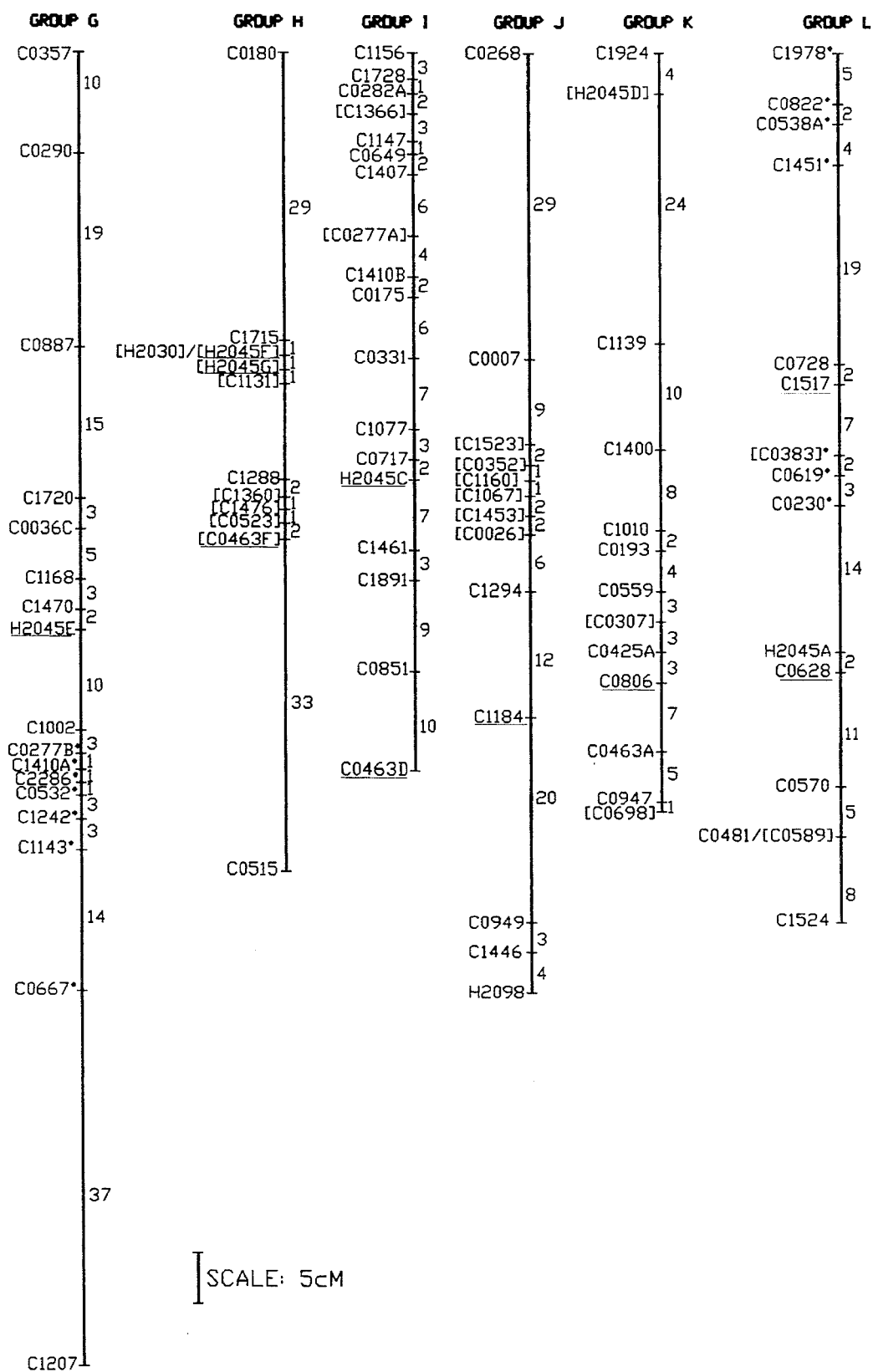
Figure 1C:
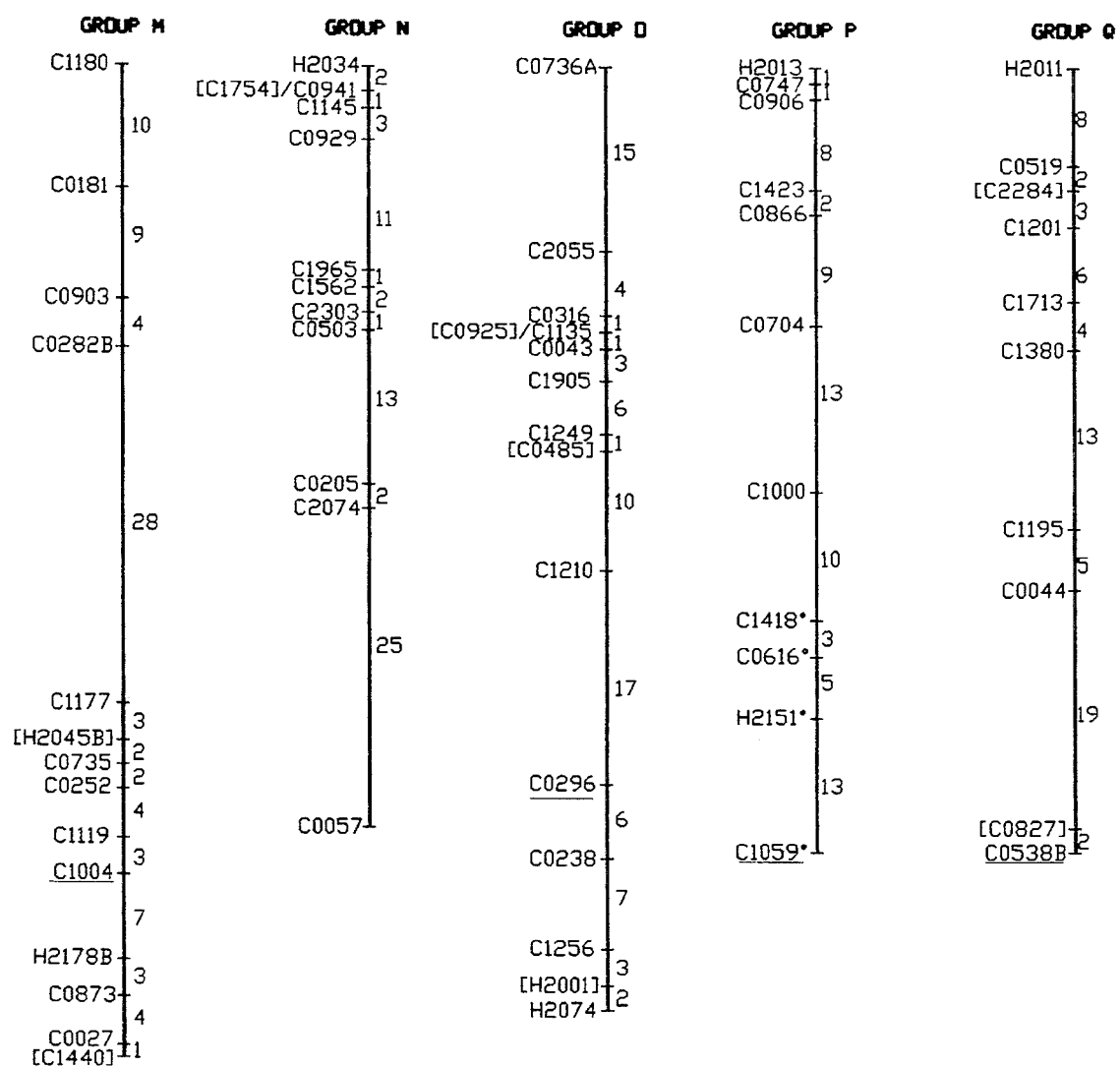

FIG. 1 shows a sunflower RFLP linkage map of 234 loci identified by 213 probes. The seventeen linkage groups are listed at the top, the loci listed on the right and the map distances in centiMorgans (cM) on the left. The nomenclature of the RFLP loci is described in "Materials and Methods". Loci mapped as dominant markers are underlined and those deviating from the expected Mendelian segregation ratios (P<0.05) are indicated with *. The loci with uncertain map positions are indicated by the square brackets. Twenty-three loci (indicated by an asterisk (*) in FIG. 1) showed distorted segregation ratios (P<0.05) all with a reduction in the ZENB8 homozygous class (Table 2).

TABLE 2

Loci showing distorted segregation (P<0.05) from the expected ratios of 1:2:1 or 3:1 (A = HA89 homozygous class, H = heterozygous class and B = ZENB8 homozygous class).

| Locus | Group | A | H | B | $\chi^2$ |
|---|---|---|---|---|---|
| C0277B | G | 81 | 147 | 52 | 6.71 |
| C1410A |   | 80 | 155 | 50 | 8.51 |
| C2286 |   | 82 | 152 | 51 | 8.01 |
| C0532 |   | 80 | 155 | 52 | 7.31 |
| C1242 |   | 75 | 161 | 49 | 9.55 |
| C1143 |   | 82 | 150 | 49 | 9.04 |
| C0667 |   | 74 | 157 | 48 | 9.24 |
| C1978 | L | 72 | 159 | 48 | 9.58 |
| C0822 |   | 72 | 153 | 48 | 8.21 |
| C0538A |   | 73 | 157 | 51 | 7.32 |
| C1451 |   | 65 | 161 | 52 | 8.18 |
| C0383 |   | 88 | 141 | 50 | 10.38 |
| C0619 |   | 88 | 145 | 51 | 9.77 |
| C0230 |   | 86 | 139 | 55 | 6.88 |
| C1418 | P | 70 | 159 | 46 | 10.91 |
| C0616 |   | 71 | 161 | 51 | 8.20 |
| H2151 |   | 67 | 164 | 54 | 7.67 |
| C1059 |   | 61 | 172 | 53 | 12.21 |
| C2246 | A | 67 | 153 | 53 | 6.12 |
| C0463B |   | ... | 226 | 51 | 6.41 |
| C0082 | B | 65 | 161 | 56 | 6.25 |
| C0463C | C | 97 | 181 | ... | 14.51 |
| C1997 | F | 63 | 152 | 50 | 7.02 |

Eighteen of these loci mapped to four regions on linkage groups G, L and P. Taking into account only the codominant markers within these regions, the HA89 and ZENB8 allele frequencies were 54% and 45%, respectively. In comparison, the allele frequency across the genome as a whole was 51% and 49% for HA89 and ZENB8, respectively.
Description of the map Analysis of the segregation data using MAPMAKER revealed that 234 loci were arranged in 17 linkage groups (FIG. 1), covering 1380 cM of the sunflower genome (Table 3).

TABLE 3

The size in centiMorgans and the number of loci in each of the 17 linkage groups.

| Group | No. of loci | Size (cM) |
|---|---|---|
| A | 20 | 109 |
| B | 19 | 88 |
| C | 13 | 76 |
| D | 11 | 52 |
| E | 11 | 90 |
| F | 10 | 88 |
| G | 17 | 129 |
| H | 12 | 83 |
| I | 18 | 71 |
| J | 13 | 90 |
| K | 13 | 74 |
| L | 15 | 84 |
| M | 14 | 81 |
| N | 12 | 62 |
| O | 15 | 76 |
| P | 11 | 65 |
| Q | 10 | 62 |
| Total | 234 | 1380 |

One locus (C0592) segregated independently. The distribution of marker loci between the different linkage groups is shown in Table 3. Linkage groups F and Q have the lowest number of mapped loci. The average map interval was 5.9 cM, however there were 11 regions on 10 linkage groups which were greater than 20 cM. In general the probes that detected duplicated regions hybridized to two unlinked loci (Table 4); however two probes H2045 and C0463 revealed loci on six different linkage groups.

TABLE 4

Sunflower RFLP probes detecting multiple loci.

| Probe | No. of loci | Groups |
|---|---|---|
| C0036 | 2 | B, G |
| C0252 | 2 | M, A |
| C0277 | 2 | G, I |
| C0282 | 2 | I, M |
| C0425 | 2 | B, K |
| C0463 | 6 | K, A, C, I, D, H |
| C0538 | 2 | L, Q |
| C0736 | 2 | O, F |
| C1161 | 2 | A, C |
| C1410 | 2 | G, I |
| H2045 | 7 | L, M, I, K, G, H |
| H2178 | 3 | D, M |

The best order of markers on each linkage group (i.e. the one which gave the highest LOD score) is given in FIG. 1; however these orders are not unequivocal. Loci whose positions are uncertain are shown in square brackets on the map because they were either placed at a LOD score of less than 3.0 or were excluded by the three-point linkage data.

The present invention includes a genetic linkage map for H. annuus, comprising 234 loci organized into 17 linkage groups (FIG. 1) which correspond to the 17 haploid chromosomes of cultivated sunflower. The letter identifying each linkage group is completely arbitrary as no classical genetic map exists for sunflower. The coverage of 1380 cM probably represents 60–80% of the sunflower genome, based on comparisons with a RAPD map constructed for H.anotnalus (an interspecific hybrid between H.annuus and H. peti-

*olaris*). The distribution of markers between the 17 groups is fairly uniform (Table 3) with, in general, the largest groups containing the most markers. The differences between the overall lengths of the linkage groups (e.g. group G is 2.5 times bigger than group D) may be related to chromosome size differences as is the case in tomato or be a factor of the incomplete sampling of the genome. Although the majority of loci are well dispersed (average interval of 5.9 cM), there are 11 regions where the distance between pairs of adjacent markers exceeds 20 cM. Similar "gaps" have been reported in most plant RFLP maps and they probably represent highly recombinogenic regions of the genome or reflect an under-representation of clones from these areas in the libraries, used as probe sources.

The majority of mapped loci were scored as codominant markers and followed the expected 1:2:1 segregation ratio in the $F_2$ population. However there were a number of loci that showed distorted segregation (Table 2) and these were found to be localized to 4 chromosomal regions on linkage groups G, L and P (FIG. 1). This distortion is thought to be due to the presence of deleterious alleles in these regions. In this study tile distorted segregation was always due to a reduction in the ZENB8 homozygous class, but in the $F_2$ populations cited above there were genomic regions showing reductions in both homozygous classes. This suggests that there was selection against the ZENB8 genome between the selfing of the $F_1$ and the flowering of the $F_2$, when the leaf tissue was harvested. Skewed distributions largely towards one homozygote is surprising.

The sunflower RFLP map reported here is being supplemented using mapping data from other $F_2$ populations. The use of cDNA clones as the primary source of probes enables the saturation of the most important areas of the sunflower genome (i.e. genic regions) and allows the dissection of quantitative traits into their component Mendelian factors.

In the next step of developing a breeding method for sunflowers the invented map was utilized as the linkage blocks on the chromosomal regions associated with high oil were identified and mapped. The following procedure was employed. A F2 population consisting of 289 individuals was produced by crossing two inbred lines that differ for the traits. RFLP and trait data were obtained directly from self-pollinated $F_2$ plants. RFLP markers (identifying 201 codominant loci) located six regions representing 57% of the genetic variation of seed oil percentage. Two of these regions were associated with kernel oil percentage, two with kernel percentage and two with both components. Additive gene action was predominant for seed oil percentage and its components.

The oil percentage in the seed is a function of kernel oil percentage, kernel weight percentage, and the hull components (Seed Oil %=[Kernel %×Kernel oil %+Hull %×Hull Oil %]/100). Kernel oil percentage, kernel weight percentage and hull oil percentage vary from 40 to 70%, 48 to 78%, and 1.6 to 6% respectively. Seed oil percentage is largely determined by the genotype of the maternal parent. Kernel oil percentage seems to have more influence on the level of seed oil percentage than does kernel percentage, and there appears to be no genetic linkage between the two components. Improvement of seed oil percentage in the hybrid progeny has been achieved by increasing seed oil percentage in the inbred progeny. This improvement has been accomplished by a reduction of the hull percentage (or increase of kernel percentage), and to a lesser extent, by an increase of the kernel oil percentage.

Seed oil percentage has relatively high broad sense heritability (0.6–0.7) and high narrow sense heritability (0.5–0.6) on a single plant basis.

Few studies have been conducted using molecular markers in sunflower. Linkage between genetic factors and RFLPs have not been reported in sunflower. This invention identifies RFLPs linked to QTL affecting oil percentage in the seed and its components, kernel oil percentage and kernel percentage. This invention permits practical breeding of improved sunflower lines. This invention includes a method of using RFLPs linked to genes affecting oil percentage in backcrossing inbred lines so that the desired trait of high oil percentage can be tracked and introgressed into lines with low oil percentage but high seed yield in specific hybrid combinations.

MATERIALS AND METHODS

Germplasm and Field Design

An $F_2$ population was used in the experiment. A cross between inbred lines ZENB8 and HA89 was made in 1990 at Venado Tuerto (Argentina) and a single $F_1$ plant was self-pollinated the following year in the same location. ZENB8 is a proprietary inbred line derived from a cross between two Argentine populations and maintained through more than 10 generations of self-pollination. HA89 is a public line released by the USDA in Fargo, N. D. The achene of ZENB8 has 33, 43, and 59% of seed oil, kernel oil, and kernel, respectively, while HA89 has 49, 56, and 77% of seed oil, kernel oil, and kernel, respectively. Both parents have normal cytoplasm and nonrestorer genes (B lines) for Leclercq's cytoplasm.

Three hundred and forty $F_2$ plants were planted in rows at Fargo, ND. Two seeds per hill were sown with a hand planter and thinned to one plant per hill. The space between rows was 75 cm and the distance between hills was 30 cm. Five rows of each parent and the $F_1$ were planted at different periods (−10, −5, 0, +5, +12 days relative to the $F_2$ planting date), to estimate the within row error variance. Before anthesis, heads were covered with pollination bags to ensure self-pollination.

RFLP Data Collection

Three leaves of each of 289 F: plants were collected in containers with dry ice and frozen at −70 ° C. Samples were lyophilized, and ground to a fine powder with a cyclone mill. A total of 198 probes (identifying 201 codominant loci) were used to locate QTL.

Evaluation of Seed Oil Percentage and its Components

The sunflower achene is a fruit consisting of a kernel (true seed) and a pericarp (hull). The kernel consists of an embryo, endosperm and a seed coat. The pericarp (maternal tissue) consists of several layers, cuticle (external layer), epidermis, hypodermis, phytomelanin layer, fibrose tissue, and finally parenchymal layers adjacent to the kernel. In the industry the word 'seed' is used synonymously with 'achene' and will so used herein.

Three seed traits were evaluated. Seed oil percentage, its components kernel oil and kernel percentage were measured in a 10 g sample of $F_3$ seed of each $F_2$ plant. The partition and components are described as follows:

Seed Oil %=[(Kernel %×Kernel oil %)+(Hull %×Hull Oil %)]/100 where,

Kernel %=[Kernel weight/total seed weight]×100

Hull %=[Hull weight/total seed weight]×100=100−Kernel

Kernel oil %=[Kernel oil weight/total kernel weight]×100

Hull oil %=[hull oil weight/total hull weight]×100

The seed samples were dried at 35° C. for 8 hours to approximately 4% moisture before analyzing the seed oil percentage in a Nuclear Magnetic Resonance Analyzer (NMR). Then, samples were manually dehulled to measure the hull and kernel weight percentages. A five-gram sample of kernel was taken to measure kernel oil percentage.

Statistical Analysis

The analysis was divided into three parts, analysis of phenotypic data, analysis of RFLP data, and combined analysis for the detection of QTL. Analyses were done with programs written in version 6.03 of SAS (SAS Institute Inc. 1988).
Phenotypic data.

Row effects were assessed with analyses of variance (ANOVA), considering rows as a source of variation (estimating phenotypic and within row variance plus among row variance), and plants within a row as an estimator of the phenotypic and within row variance. Significant row effects were not detected (P>0.05) for any trait.

Simple-Pearson phenotypic correlations between seed oil percentage and its components were calculated to estimate the relationship between traits. To estimate the total phenotypic variability due to genetic effects, broad sense heritabilities ($h^2$) were calculated. The within-row variance was estimated by pooling within-row variances of the parent and $F_1$ rows. The error variance among rows was estimated in the $F_2$ population. The genetic variation was then estimated subtracting the within and among variances from the phenotypic variance.
RFLP data analysis.

The genetic map was constructed. Results showed that genotypic classes at 23 loci deviated significantly from the expected ratios. Those loci exhibited a reduction in the ZENB8 homozygous class. The majority of the loci (18/23) were found to map to four regions, representing linkage groups G', L' and P'.

The genomic composition of each $F_2$ plant was determined from the frequencies of each genotypic class (homozygous ZENBS, heterozygous, homozygous HA89) across all loci. Frequencies of each class were the number of loci having each genotypic class divided by the total number of loci scored for each plant. The average genomic composition of the $F_2$ population was determined as the average value for each class across the population.
Detection of QTL For each trait, single factor analyses of variance were conducted within RFLP-loci for the genotypic classes and their trait value. F-tests were used to determine if significant variation in trait expression was associated with the marker-locus genotypic classes. Significant F-values provide evidence of linkage between a QTL and a marker locus. Evidence of linkage was declared when the F-test at any locus for any trait gave a probability lower than 1%. In addition, whenever the F-test for seed oil percentage had a probability lower than 5%, and any of its components at the same region was also lower than 5%, linkage was indicated. This criterion was established because the probability of having two false positives (at the 5% level) located in the same genomic region is lower than 5% when the two traits are not completely correlated (r=1). At the stated per locus error rate (1%) the probability of having at least one false positive across the genome (type I error) is 87%.

For those loci where F-tests were statistically significant, additive and dominant effects were calculated as is known in the industry. Loci with highest significant F-tests within regions of several closely linked RFLP loci were selected as flanking markers. Additive effects for the interval between flanking markers were determined as the sum of the two partial regression coefficients for the regression of trait values on flanking markers. The sum of the regression coefficients for the two flanking markers estimates the additive effect of a QTL located in the interval. The d/a ratio scale described by Edwards et al. (1987) was used to classify gene action. The d/a ratio was calculated by dividing the dominant(d) to additive(a) effects of the marker(s) significantly linked to the QTL.

Multiple regression analysis was conducted to estimate phenotypic variation explained by additive effects. An independent variable ($Q_i$) was created based on the weight of each partial regression coefficient on marker classes (AA, Aa, aa; coded 10–1, respectively). The dependent variables were the seed trait values. The coefficient of determination ($R^2$) for multiple regression estimates the proportion of variation accounted by the model. This regression model estimates the sum total of additive effects. This $R^2$ was compared with the estimated broad sense heritability to calculate the amount of genetic variation accounted by the regression.

For detection of epistatic effects, two-way Analyses of Variance were conducted for those loci with significant F-tests for seed oil percentage. Pairs of markers were taken and the interlocus interaction variance was partitioned into additive×additive, additive×dominance, dominance×additive and dominance×dominance interactions.

RESULTS

Phenotypic data

Trait means for the parents, $F_1$ and $F_2$ progeny are presented in Table 5. Inbred HA89 seed oil percentage exceed that of ZENB8 by 19 percentage points. This difference is reflected by the higher kernel oil and kernel percentages of HA89. In the $F_2$ progeny, the distribution of all traits did not fit a normal distribution ($\alpha$:0.05). Coefficients of Skewness ($\gamma_1$) for seed oil percentage, kernel oil percentage, and kernel percentage, were −0.54, −0.42, and −0.54, respectively. In all cases the skewness was towards low values. Transgressive segregants were not detected for seed oil percentage. The seed oil percentage of the $F_2$ plants was within the range of the parents' mean values. Broad sense heritabilities were 0.47, 0.29, and 0.41, for seed oil percentage, kernel oil percentage, and kernel percentage, respectively (Table 5).

TABLE 5

Trait means, variance components and broad sense heritabilities.

| Material | Seed oil % | Kernel oil % | Kernel % |
|---|---|---|---|
| ZENB8 | 33 ± 1.4† | 50 ± 2.0 | 56 ± 1.4 |
| HA89 | 52 ± 2.7 | 60 ± 2.2 | 72 ± 2.7 |
| $F_1$ | 46 ± 2.8 | 57 ± 2.1 | 70 ± 2.8 |
| $F_2$ | 44 ± 0.5 | 56 ± 0.5 | 69 ± 0.6 |
| Variance Components | | | |
| $\delta^2 p$‡ | 18.31 | 13.52 | 20.28 |
| $\delta^2 g$§ | 8.66 | 3.94 | 8.26 |
| $\delta^2$¶ | 9.65 | 9.58 | 12.02 |

TABLE 5-continued

Trait means, variance components and broad sense heritabilities.

| Material | Seed oil % | Kernel oil % | Kernel % |
|---|---|---|---|
| $h^2$# | 0.47 | 0.29 | 0.41 |

†Mean ± 2 Standard errors of mean (day 0, relative to $F_2$ planting)
‡Phenotypic variance
§Genotypic variance
¶Experimental error variance
Broad sense heritability Kernel oil percentage and kernel percentage were positively correlated with seed oil percentage (0.82 and 0.47, respectively). The correlation between these two components was 0.33.

RFLP data analysis

Figure 2A:
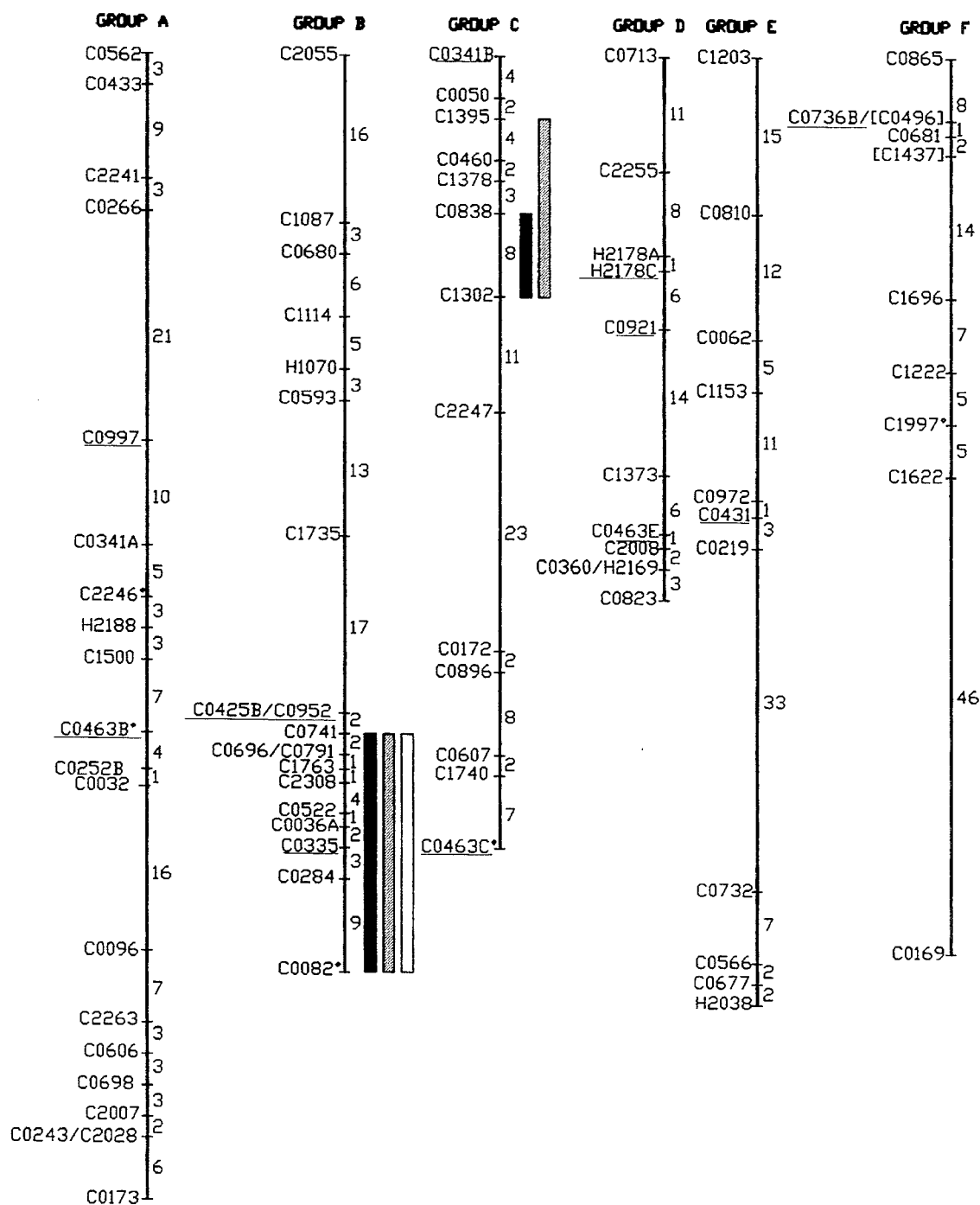
FIGS. 2A, 2B, 2C Shows a RFLP linkage map and distribution of QTL. The seventeen linkage groups are listed at the top, loci on the left and map distances (cM) on the right. Loci mapped as dominant markers are underlined and those deviating from the expected segregation ratios (P<0.05) are indicated with an asterisk (*). The QTL affecting seed oil percentage (black blocks), kernel oil percentage (shaded blocks) and kernel percentage (white blocks) are located to the right of respective linkage group.
Figure 2B:
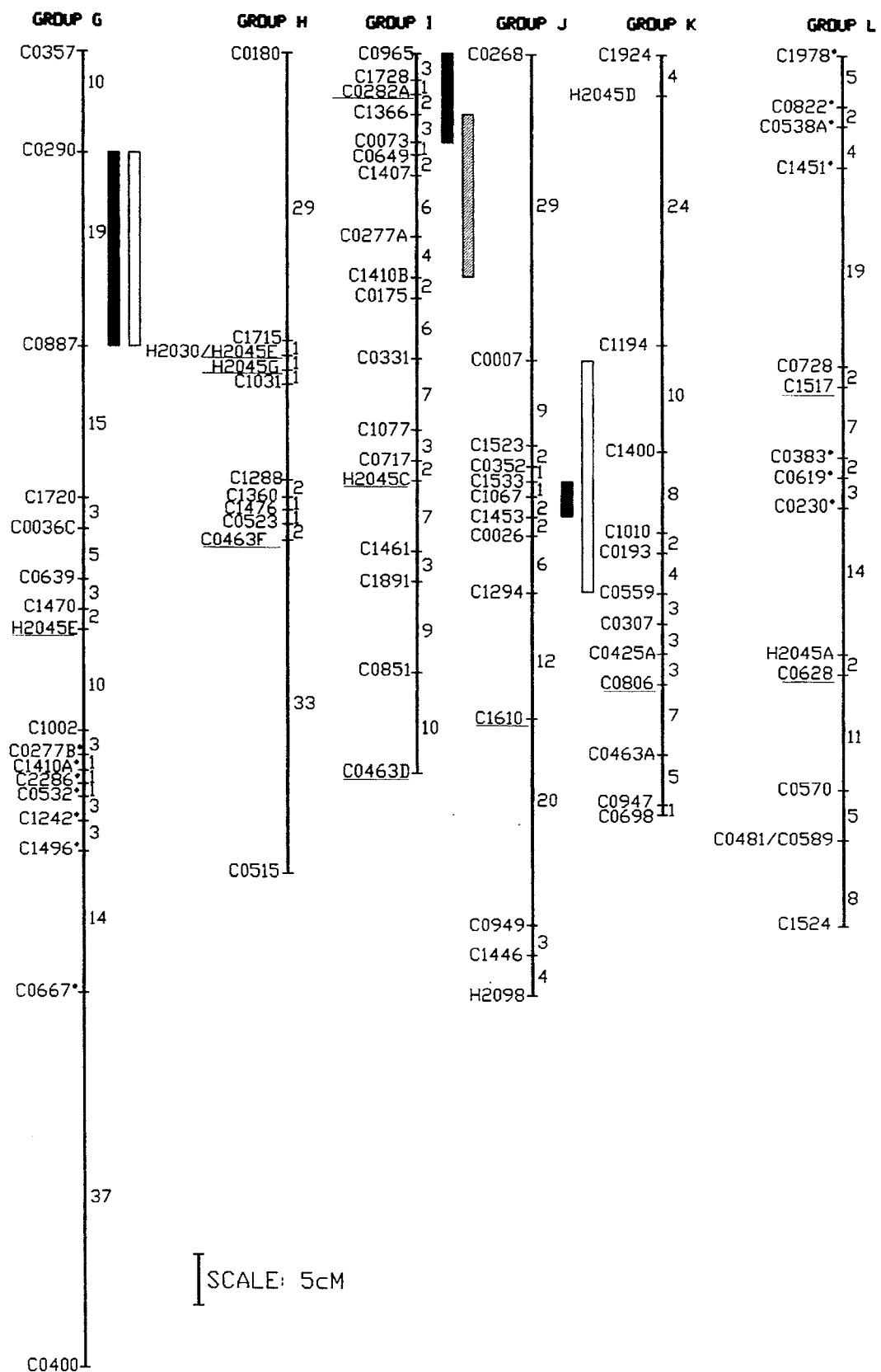
Figure 2C:
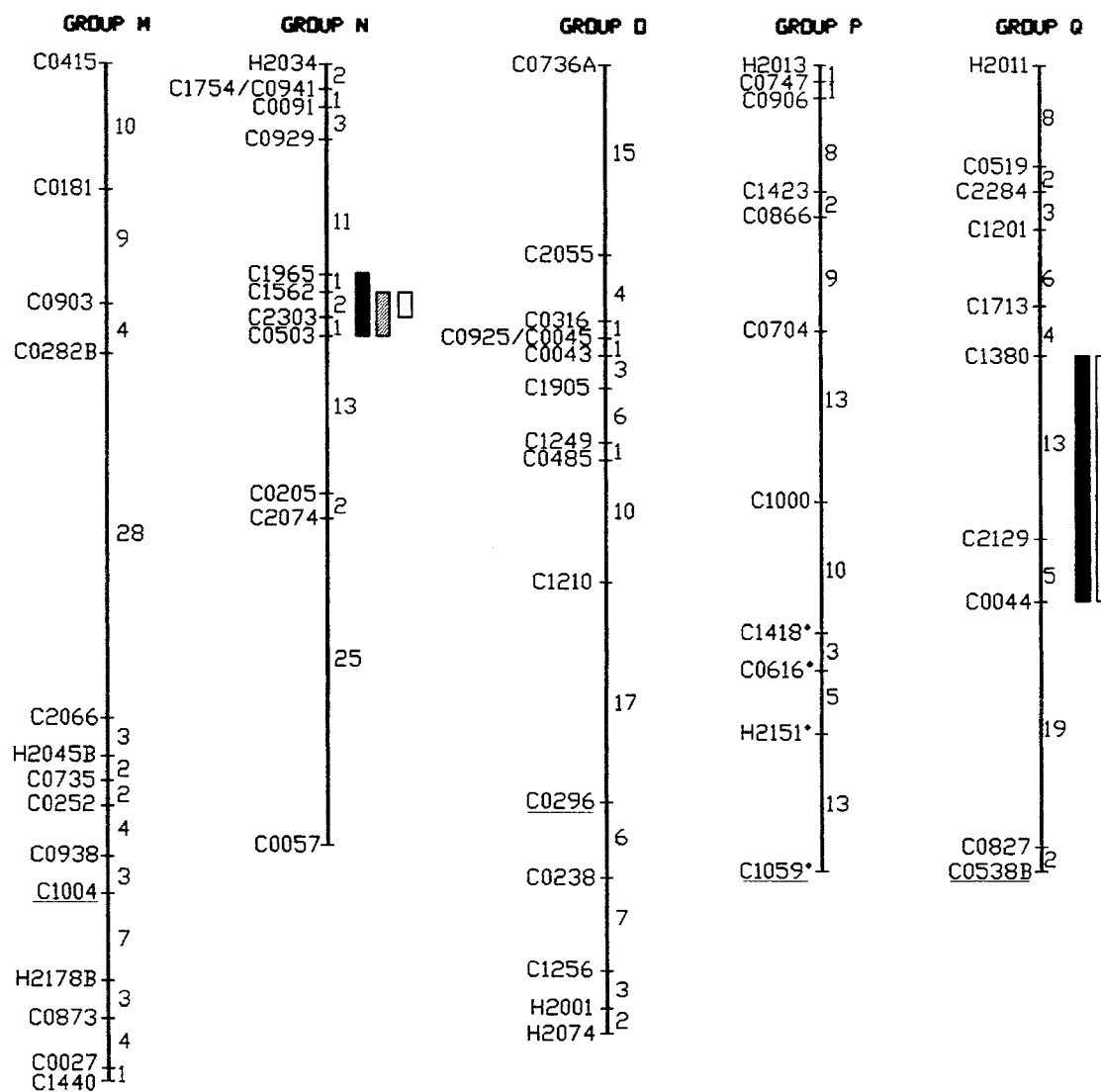
Figure 3:
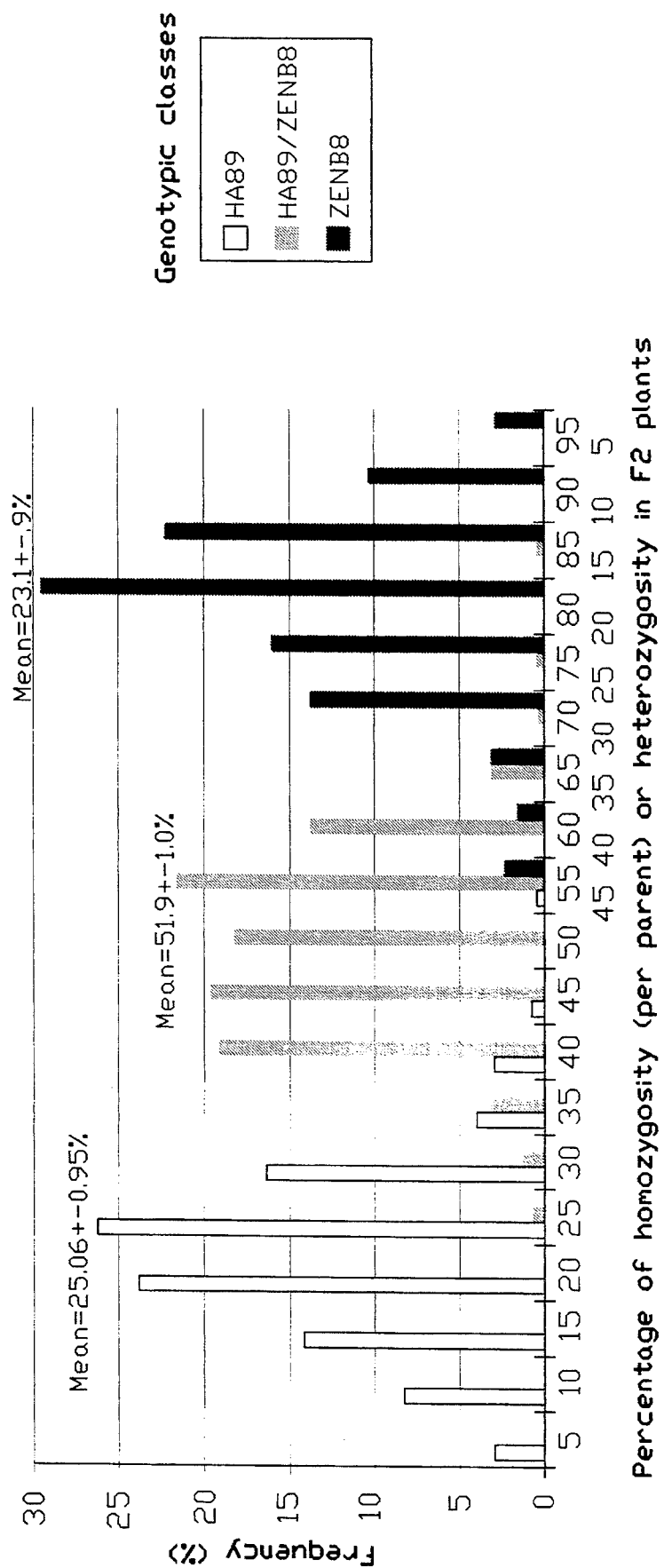
FIG. 3 Average genomic composition of $F_2$ plants.

The RFLP linkage map used for this is shown in (FIG. 2). FIG. 2 shows a RFLP linkage map and distribution of QTL. The seventeen linkage groups are listed at the top, loci on the left and map distances (cM) on the right. Loci mapped as dominant markers are underlined and those deviating from the expected segregation ratios (P<0.05) are indicated with an asterisk (*). The QTL affecting seed oil percentage (black blocks), kernel oil percentage (shaded blocks) and kernel percentage (white blocks) are located to the right of respective linkage group. The average genomic composition of the $F_2$ population is shown in FIG. 3. The composition of individual $F_2$ plants homozygous for HA89 or ZENB8 alleles ranged from 5.1 to 57.4%, or 5.4 to 47.5%, respectively. The allele frequency across the genome was 51% and 49% for HA89 and ZENB8, respectively.

The mean seed oil percentage mean for the highest and lowest ten percent (standardized selection intensity (i)=1.76) of plants having the highest (>49.5%) and lowest (<38.0%) seed oil percentage was 50.7 and 35.5%, respectively. ZENB8 allele frequency across the entire genome ranged from 25 to 57% and 36 to 66% for the selections with highest and lowest oil percentage, respectively. The ZENB8 allele frequency across regions unlinked to QTL associated with seed oil content ranged from 31 to 57% and 32 to 64% for the selections for high and low seed oil percentage, respectively.

Detection of QTL

Overall, seven regions were significantly associated with seed oil percentage or one of its components; however most regions were significantly associated with more than one trait (Table 6). In the majority of these regions, additive effects were more important than non-additive.

TABLE 6

Loci detecting significant variation for seed oil, kernel oil and kernel percentages.

| Linkage group | Locus | Seed oil % | | Kernel oil % | | Kernel % | |
|---|---|---|---|---|---|---|---|
| | | P>F | $R^2$† | P>F | $R^2$† | P>F | $R^2$† |
| B | C0952 | **** | 0.10 | **** | 0.09 | * | 0.03 |
| B | C0741 | **** | 0.13 | **** | 0.13 | ** | 0.05 |
| B | C0696 | **** | 0.13 | **** | 0.12 | ** | 0.06 |
| B | C0791 | **** | 0.13 | **** | 0.13 | ** | 0.05 |
| B | C1763 | **** | 0.14 | **** | 0.13 | ** | 0.05 |
| B | C2308 | **** | 0.15 | **** | 0.13 | ** | 0.05 |
| B | C0522 | **** | 0.12 | **** | 0.13 | * | 0.03 |
| B | C0036A | **** | 0.11 | **** | 0.10 | ** | 0.05 |
| B | C0284 | **** | 0.13 | **** | 0.11 | ** | 0.04 |
| B | C0082 | **** | 0.09 | **** | 0.08 | *** | 0.07 |
| C | C1395 | | 0.01 | * | 0.03 | | 0.01 |
| C | C1302 | * | 0.03 | * | 0.03 | | 0.01 |
| G | C0357 | * | 0.03 | | 0.01 | | 0.01 |
| G | C0290 | **** | 0.08 | | 0.01 | ** | 0.05 |
| G | C0887 | **** | 0.11 | | 0.01 | ** | 0.05 |
| G | C1720 | ** | 0.04 | | 0.01 | | 0.01 |
| I | C0985 | * | 0.03 | * | 0.04 | | 0.00 |
| I | C1728 | * | 0.03 | * | 0.04 | | 0.00 |
| I | C1366 | * | 0.03 | ** | 0.05 | | 0.00 |
| I | C0073 | * | 0.03 | * | 0.04 | | 0.00 |
| I | C0649 | | 0.01 | * | 0.03 | | 0.01 |
| I | C1407 | | 0.02 | * | 0.03 | | 0.01 |
| I | C0277A | | 0.01 | * | 0.03 | | 0.01 |
| I | C1410B | | 0.01 | ** | 0.04 | | 0.02 |
| I | C0175 | | 0.01 | * | 0.03 | | 0.02 |
| | | Seed oil % | | Kernel oil % | | Kernel % | |
| Group | Marker | Prob. | $R^2$† | Prob. | $R^2$† | Prob. | $R^2$† |
| J | C0007 | | 0.02 | | 0.00 | * | 0.03 |
| J | C1523 | | 0.02 | | 0.00 | * | 0.03 |
| J | C1533 | * | 0.03 | | 0.01 | ** | 0.04 |
| J | C1067 | * | 0.03 | | 0.00 | * | 0.04 |
| J | C1453 | * | 0.03 | | 0.00 | ** | 0.04 |
| J | C0026 | | 0.02 | | 0.00 | * | 0.03 |
| J | C1294 | | 0.01 | | 0.01 | ** | 0.05 |
| N | C1965 | *** | 0.07 | * | 0.04 | | 0.02 |
| N | C1562 | ** | 0.05 | | 0.02 | * | 0.03 |
| N | C2303 | *** | 0.07 | * | 0.04 | * | 0.03 |
| N | C0503 | * | 0.04 | | 0.02 | | 0.02 |
| Q | C1713 | | 0.01 | * | 0.03 | | 0.01 |
| Q | C1380 | | 0.01 | * | 0.03 | | 0.01 |
| Q | C2129 | | 0.01 | ** | 0.05 | | 0.00 |
| Q | C0044 | | 0.01 | * | 0.04 | | 0.00 |

*, , *, ****: Significance level of 0.05, 0.01, 0.001 and 0.0001 respectively.
†Coefficient of determination ($R^2$). Amount of variation explained by each marker.

For kernel percentage, nineteen percent of the phenotypic variation (Table 7) was explained by four QTL (FIG. 2).

TABLE 7

Location, genetic effects and contribution of the regions controlling oil percentage.

| Trait | Linkage group | $R^2$ | $R^2$† | Additive‡ effect | High parent | d/a§ | Gene¶ action |
|---|---|---|---|---|---|---|---|
| | | | | oil % | | | |
| Kernel % | B | 0.07 | | −2.25 | HA89 | +0.15 | A |
| | G | 0.05 | 0.19 | −1.67 | HA89 | −0.68 | D |
| | J | 0.04 | | 1.57 | ZENB8 | +0.68 | D |
| | N | 0.03 | | −1.09 | HA89 | +0.10 | A |
| Kernel oil % | B | 0.10 | | −2.20 | HA89 | +0.42 | A |
| | C | 0.02 | | −0.86 | HA89 | +0.34 | A |
| | I | 0.05 | 0.20 | −1.17 | HA89 | −0.06 | A |
| | N | 0.03 | | 0.00 | — | −4.50 | OD |
| | Q | 0.04 | | −1.21 | ZENB8 | +0.19 | A |
| Seed oil % | B | 0.13 | | −2.98 | HA89 | +0.39 | A |
| | C | 0.01 | | −0.65 | HA89 | +1.49 | OD |
| | G | 0.12 | 0.27 | −2.53 | HA89 | −0.24 | A |
| | I | 0.01 | | −0.59 | HA89 | +1.64 | OD |
| | J | 0.03 | | 1.14 | ZENB8 | −0.28 | A |
| | N | 0.02 | | −0.81 | HA89 | −2.47 | OD |

†Amount of variation explained by all DNA regions with significant F test.
‡Negative sign means an increase of the mean value of the trait due to HA89 alleles. A positive sign means an increase of the mean value of the trait due to ZENB8 alleles.
§Ratio of the average dominant and additive effects of the markers located within a significant region. A positive sign means dominance for higher value of the trait. A negative sign means dominance for lower value of the trait.
¶A = additive or partial dominance, D = partial dominance or dominance, OD = overdominance. Based on the scale of the ratio d/a reported by Edwards et al. (1987.).

Individually, QTL accounted for three to seven percent of the phenotypic variation. Additive effects in all regions, and additive gene action in two of the four regions seems to control the expression of the trait. Dominance or partial dominance gene action was detected in the other two regions.

For kernel oil percentage five unlinked regions (FIG. 2) explained twenty percent of the phenotypic variation (Table 7). A region with major effects was located to linkage group B' that accounted for 10% of the variation. Other significant regions explained less than five percent. Additive gene effects were present in almost all regions except in linkage group N'. The ratio d/a indicated that kernel oil percentage was mainly controlled by additive gene action; although, the region in linkage group N' exhibited overdominance for lower kernel oil percentage.

Alleles at six genomic regions were significantly associated with seed oil percentage. QTL were located in regions affecting kernel oil percentage and/or kernel percentage (FIG. 2). These regions accounted for 27% of the phenotypic variation, with regions in linkage groups B' and G' having the largest contributions, 13% and 12% respectively (Table 7). When only these two regions were included in the multilocus analysis, they accounted for 23% of the phenotypic variation. Other regions explained between 3 and 1%. Intralocus interactions were detected in three regions with overdominance gene action for higher or lower seed oil percentage. Epistatic effects between pairs of marker loci were not statistically significant.

Additive effects for higher values of seed oil percentage, kernel oil percentage, and kernel percentage were usually derived from the alleles of the parent with highest oil percentage (HA89) (Table 3). In one region (linkage group J') alleles from ZENB8 increased the seed oil percentage.

Significant QTL were found in this experiment for all traits. Six genomic regions controlling seed oil percentage and at least one of the seed oil components were identified.
Heritability and genetic variance explained by QTL Heritability of seed oil percentage (Table 5) was lower than previously reported values (0.6–0.7) for individual $F_2$ plants.

Broad-sense heritability estimates the phenotypic variation due to genetic sources. Thus, the maximum phenotypic variation that multiple loci analysis can explain is the estimate of heritability. The coefficient of determination ($R^2$) in the multiple loci analysis of regions associated with seed oil, kernel oil and kernel percentages explained 27%, 20%, and 19% of the phenotypic variation, respectively (Table 7). When comparing these values with the heritability of the traits, the QTL explain 57%, 69% and 46% of the genetic variation for seed oil, kernel oil and kernel percentage, respectively. Dominance and genotypic by environment interaction are included in the estimation of the genetic variance, while only additive effects are included in the sum of the regression coefficients of the flanking markers. Thus, the genetic variation probably underestimates the real importance of the six regions and perhaps other regions, since it does not account for dominant or interaction effects.

Phenotypic correlation and QTL localization

Consistent with prior observations the seed oil components kernel oil and kernel percentage were positively correlated with oil percentage in the whole seed. The higher correlation of seed oil percentage with kernel oil percentage than with kernel percentage suggests that kernel oil percentage has more influence in the determination of seed oil percentage.

Phenotypic correlations between traits are determined by genetic or environmental correlation. The sources of genetic correlations are pleiotropy or linkage. For the six regions controlling seed oil percentage (FIG. 2) two were associated with kernel oil percentage (linkage groups C' and I'), two with kernel percentage (linkage groups G' and J') and the other two with both traits (linkage groups B' and N'). As kernel oil and kernel percentage are components of the seed oil percentage, the coincidence in QTL localization suggests pleiotropic effects. This effect could be responsible for the degree of correlation reported between both kernel oil and kernel percentages with seed oil percentage. However, it is impossible to discern if the positive correlation (0.33) between kernel oil and kernel percentages was due to linkage or pleiotropic effects (linkage groups B' and N' ) in this study. Contrary to a previous report by Dedio, (1982), in this population, regions controlling both traits were genetically associated.

Gene action and effects

Additive effects mainly control the expression of seed oil percentage and its components (Table 7). Although three regions showed overdominance for seed oil percentage, the means of the homozygous HA89 and heterozygous classes are not statistically significant at the 5% level, at two regions (linkage groups (C' and I'). Thus, in these two regions it is more likely that gene action is dominance rather than overdominance. Also, gene action for kernel oil percentage in these regions is additive or partially dominant. The fact that dominant or overdominant gene action was associated with the regions with lowest additive effects also suggests that additive effects are much more important than non-additive effects. This is also supported by the small difference in mean seed oil percentage between the $F_1$ and $F_2$ progeny. Moreover, the increase in the oil percentage in hybrid progeny through selection in inbred progeny could probably be explained by the relative importance of additive effects in the expression of seed oil percentage.

Genomic composition and utility for breeding

A backcross program to improve the seed oil percentage in ZFNB8 can improve only one of its components without affecting the other. The backcross progeny does not include regions in linkage groups where both components are genetically associated (i.e., groups B' and N'). Because region B' is associated with almost half of the genetic variability, then the potential genetic gain would be reduced; assuming components are genetically associated due to pleiotropic effects.

The resources spent determining genomic composition of individuals or families for mapping QTL can be utilized by using the data to help conventional breeding with selection among families. The information could be useful to select for diversity across families to initiate testcrosses, level of homozygosity, and degree of relationship with one of the parents. Among the ten percent (i=1.76) of plants having the highest oil percentage (mean=50.7%), there is enough variation in ZENB8 allele frequency across the entire genome (0.25–0.57) or across regions unlinked to oil QTL (0.31–0.57) to use the RFLP genotype for background selection.

In summary, Six genomic regions explaining 57% of the genetic variation of seed oil percentage were found. Of these, two were associated with kernel oil percentage, two with kernel percentage and two with both components. Additive effects were found to be more important than non-additive effects in the expression of seed oil percentage and its components. The simultaneous study of seed oil percentage components seems to help localize QTL and improve our understanding of seed oil percentage.

The next step was the discovery of the link between seed color and high oil content. The identification of the chromosomal regions and linkage blocks associated with both the seed color (which permits visual screening of plants) and with high oil were mapped and utilized to breed improved high oil inbred sunflowers. The following procedure was employed. Sunflower seed color was determined by pigmentation of three layers of the sunflower pericarp (hull), epidermis, hypodermis, and phytomelanin layer. Although a major gene was reported controlling the inheritance of color in pigmented hypodermis, the inheritance of pigmented versus unpigmented hypodermis was not reported. The present invention identifies RFLP markers linked to factor(s) affecting seed hypodermis pigmentation and identifies the relation between this trait and oil percentage in the sunflower seed. An $F_2$ single-cross population was produced from inbred parents that differed for the traits. Two hundred sixty seven $F_2$ plants and their $F_3$ families were evaluated. A dominant factor (Hyp) controlling the presence of white pigments in the hypodermis was located to linkage group G'. Seeds with white hypodermis had lower oil percentage than those with unpigmented hypodermis. The Hyp factor was found located in the same map interval region as one QTL with major effects on with seed oil percentage.

Seed color

The pericarp color is determined by the pigmentation of the epidermis, hypodermis, and phytomelanin layer. The epidermis layer can be uniformly unpigmented or have black or dark brown pigmented stripes of varying thickness. Below the epidermis, the hypodermis can also be either completely unpigmented or pigmented (white or purple). If the third layer (phytomelanin layer) is present it has uniform dark brown-black pigments.

Genetic studies have identified factors with qualitative effects on pigment development in the hypodermis. A dominant gene T was reported controlling the presence of anthocyanin pigments in the hypodermis. Mosjidis (1982) reported that a major dominant gene (C) must be present to have purple color in that layer, and two complementary genes (Y and P) gave different intensity of purple pigmentation. Leclercq (1979) reported a single dominant gene (Gb) controlling seed color but it was not specified in his report which layer was being studied.

Relation between seed color and oil percentage

It has been discovered that seed color can be a genetic marker for selecting high oil seeds when the parents of a population differ in seed hypodermis color. As previously noted, six genomic regions controlling the expression of seed oil percentage have been located with RFLPs. All these regions were also significantly associated with at least one of the seed oil components.

Molecular markers

The present invention identifies RFLP markers linked to region(s) controlling the expression of pigmentation in the hypodermis, and compares their location with those QTL reported for seed oil percentage.

MATERIALS AND METHODS

Germplasm and Field Designs

The population used in this study was created by crossing inbred lines ZENB8 and HA89. One F1 plant was self pollinated to produce the $F_2$ generation. Three hundred and forty $F_2$ plants were grown in Fargo, ND and self pollinated to produce $F_3$ families. Two hundred sixty seven $F_3$ families were evaluated in one replication of a completely randomized design. Families were grown in single row plots 3 m long and 0.70 m wide. Rows were planted and thinned to 10 pl/row (47000 plants/ha).

ZENB8 is a proprietary inbred line derived from a cross between two Argentine populations and maintained through more than 10 generations of self-pollination. It has low seed oil percentage (33%) and white seed color (white hypodermis with black phytomelanin layer) with black stripes. HA89 is a line released by the USDA in Fargo, N. D and has high seed oil percentage (49%) and gray seed color (unpigmented hypodermis with black phytomelanin layer) with black stripes in the epidermis layer. Both parents have normal cytoplasm and nonrestorer genes (B lines) for Leclercq's cytoplasm.

Trait Characterization

Characterization of hypodermis color and oil percentage were accomplished using the seed harvested from each $F_2$ plant. $F_3$ generation data were collected from a bulk of seed (equal volume from each plant) harvested from the ten $F_3$ plants. $F_2$ plants and $F_3$ families were placed into classes according with the presence or absence of white pigments in the hypodermis. Classes of $F_2$ plants were 'white pigmented' and 'unpigmented hypodermis'. For $F_3$ families, classes were 'white pigmented', 'unpigmented' and 'segregating'. Unpigmented hypodermis was declared when gray color was observed between the black stripes of the epidermis. The 'segregating' class consist of seeds with white and unpigmented hypodermis in the bulked sample of the $F_3$ plants.

Seed oil percentage was determined with a Nuclear Magnetic Resonance Analyzer (NMR). A twelve gram sample of seed was taken from each $F_2$ plant or the bulk of $F_3$ plants. Samples were dried to 35° C. for 8 hours to approximately 4% moisture, then 10 g samples were used for the seed oil percentage determination.

Statistical Analysis

Number of factor(s) and localization

At RFLP loci exhibiting significant association, additive and dominant effects were determined from differences between mean trait values of marker locus genotypic classes. Within groups of closely linked RFLP loci, those showing the highest significant F-tests were selected as flanking markers for the factor locus. The d/a scale described by Edwards et a. (1987) was used to classify gene action of the factor(s). The d/a ratio was calculated dividing the estimated dominant(d) to additive(a) effects of the factor.

MAPMAKER computer program was used to estimate the distance (r) between the flanking markers and the factor affecting hypodermis pigmentation. Hypodermis pigmentation classes of $F_3$ families were used as morphological marker classes (codominant marker) and placed with a LOD score of 3.0 and a recombination value of 0.35 cM.

Relation between seed hypodermis color and oil percentage

Single factor analyses of variance (ANOVA) were conducted for the hypodermis pigmentation classes and their seed oil percentage. F-test were used to determine if significant variation in seed oil content was associated with the hypodermis pigmentation classes. Among $F_2$ plants, the difference between the two classes (white pigments vs. unpigmented hypodermis) was tested with F test ($\alpha$: 0.05). In $F_3$ families, differences among the three classes (uniformly white pigments, segregating, and uniformly unpigmented hypodermis) were tested with F-test, and differences between pair of classes were tested with the Least Significant Difference (LSD; $\alpha$:0.05).

RESULTS AND DISCUSSION

Linkage analysis for hypodermis color

Characterization of the trait for the different progenies is presented in Table 8.

TABLE 8

Summary and analysis of segregation for hypodermis pigmentation among $F_2$ plants and $F_3$ families.

| Generation | Number of observations | Hypodermis pigmentation | | | Expected ratio | $\chi^2$† |
| --- | --- | --- | --- | --- | --- | --- |
| | | White | Segregating | Unpigmented | | |
| $F_2$ | 267 | 212 | — | 55 | 3:1 | 2.53 |
| $F_3$ | 255 | 74 | 131 | 50 | 1:2:1 | 4.72 |

†$\chi^2$ (0.05) tabular is 3.83 for $F_2$ and 5.99 for $F_3$.

For the hypothesis of one dominant factor model Chi-square tests were used to determine the correctness of fit of the observed numbers of each hypodermis class and the expected 3 (white pigmented): 1 (unpigmented) ratio for an $F_2$ generation. The observed number of each class in $F_3$ families was tested to the expected ratio 1 (white): 2 (segregating): 1 (unpigmented). Since there is only one degree of freedom for the Chi-square tests in the $F_2$ generation a correction factor (−0.5) was applied.

The possible number of factors controlling the presence of white pigments was also estimated using ANOVA. Single factor analyses of variance were conducted within marker loci for the genotypic classes and hypodermis color (coded 0, 0.75, and 1; for unpigmented, segregating, and white pigmented, respectively). Evidence of linkage between an RFLP locus and a factor controlling pigmentation in the hypodermis was indicated when the F test gave a probability lower than 0.01. Coefficient of determination ($R^2$) for each marker locus was calculated as the ratio of the sum of squares accounted for by the RFLP classes and the total sum of squares.

Segregation of hypodermis pigmentation among $F_2$ plants and $F_3$ families fit the expected ratios for a single dominant factor. White pigmented hypodermis showed dominance over unpigmented. Concordant with this results, single factor analyses of variance identified one highly significant (P<0.0001) region associated with inheritance of hypodermis pigmentation (Table 9).

TABLE 9

Summary of single factor analysis of variance in a region in linkage group 'G'.

| Progeny | Locus | P>F | $R^2$† | a‡ | d§ |
| --- | --- | --- | --- | --- | --- |
| | | | | units | |
| $F_2$ plants | C0357 | 0.0001 | 0.40 | 0.33 | 0.30 |
| | C0290 | 0.0001 | 0.65 | 0.42 | 0.37 |
| | C0887 | 0.0001 | 0.37 | 0.30 | 0.24 |
| | C1720 | 0.0001 | 0.16 | 0.20 | 0.14 |
| $F_3$ families | C0357 | 0.0001 | 0.48 | 0.33 | 0.35 |

TABLE 9-continued

Summary of single factor analysis of variance in a region in linkage group 'G'.

| Progeny | Locus | P>F | R²† | a‡ | d§ |
|---------|-------|-----|-----|-----|-----|
|  | C0290 | 0.0001 | 0.70 | 0.42 | 0.38 |
|  | C0887 | 0.0001 | 0.42 | 0.32 | 0.24 |
|  | C1720 | 0.0001 | 0.19 | 0.21 | 0.17 |

†Coefficient of determination.
‡Additive effect. A positive sign means an increase of the mean value of the trait due to ZENB8 alleles.
§Dominant effect. A positive sign means dominance for white pigmented hypodermis.

Results from both progenies showed that C0290 is probably the closest RFLP locus to the factor since it has the highest coefficient of determination (0.70), additive and dominant effects. It is also possible to predict that the most likely position of the factor is within the interval C0290–C0887 than in C0357–C0290. Since C0357 and C0887 have $R^2$ of similar magnitude, with similar additive and dominant effects, it is expected that the location of the factor is midway between these two markers and this position is in the interval C0290–C0887.

Figure 4:
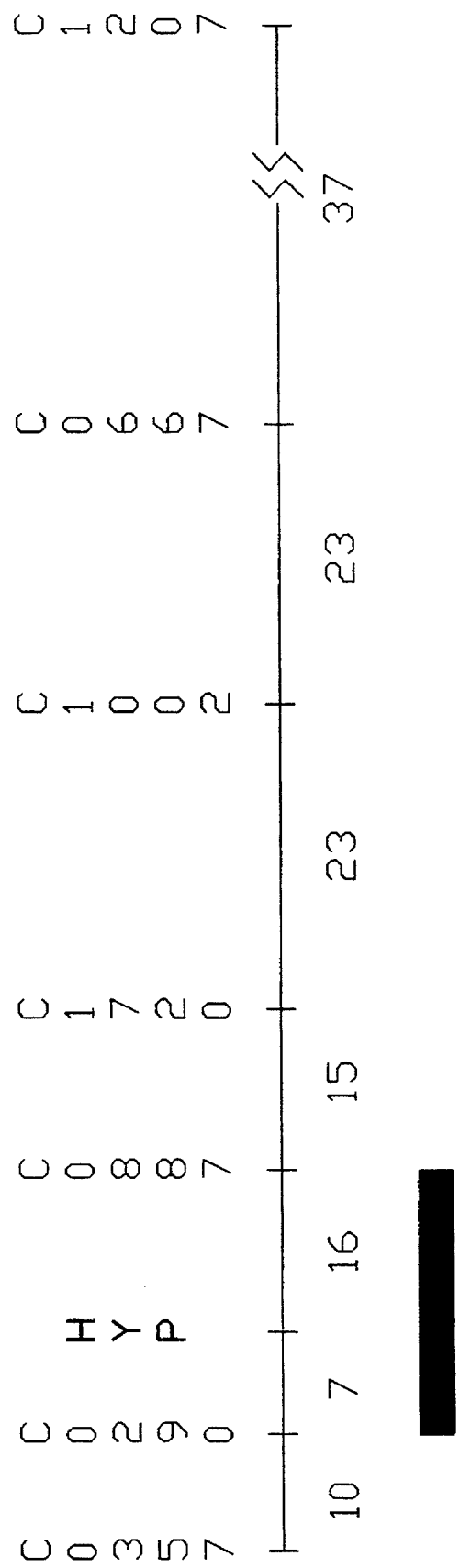
FIG. 4 Localization of Hyp locus in linkage group 'G'. Numbers represent distances (cM) between markers. Black block shows the localization of a QTL controlling seed oil percentage.

Since this phenotype seems to be controlled by one factor, it was used as a codominant morphological marker to locate its position. Three point linkage analysis (MAPMAKER) placed the Hyp factor loci at 7.4 cM from C0290 and at 15.5 cM from C0887 (FIG. 4). FIG. 4. Localization of the Hyp locus place it in linkage group G'. Numbers represent distances (cM) between markers. Black block shows the localization of a QTL controlling seed oil percentage according with previous research. In the RFLP map the interval between these two markers was 19 cM. With the placement of the Hyp marker loci the distance changes to 22.9 cM. This kind of difference is expected due to the inability to measure double crossovers between C0290 and C0887 without having a marker in the interval.

A d/a ratio of almost '1' also indicated that dominant gene action controls the expression of white pigments. Effects for the presence of whim pigments in the hypodermis are coming from the parent with white hypodermis color (ZENB8). In other words unpigmented hypodermis is a recessive trait, and alleles are coming from HA89.

The presence or absence of pigments in the hypodermis is controlled by one factor and both lines carry alleles for whim pigments at another locus, or there is an allelic series at this locus that produces anthocyanin pigments, white pigments or unpigmented hypodermis.

Relation between seed hypodermis color and oil percentage

Differences in seed oil percentage among hypodermis pigmentation phenotypes was highly significant when evaluated in $F_2$ plants and their $F_3$ progeny (Table 10).

TABLE 10

Seed oil percentage in seed with different hypodermis pigmentation.

| Progeny | Hypodermis pigmentation | Oil %† | LSD‡ |
|---------|-------------------------|--------|------|
| F₂ plants | Unpigmented | 46.5 ± 1.0 |  |
|  | White | 43.4 ± 1.0 |  |
| F₃ families | Unpigmented | 43.3 ± 0.6 | a |
|  | Segregating | 40.6 ± 0.6 | b |
|  | White | 39.4 ± 0.6 | c |

†Mean ± 2 standards error of the mean.

TABLE 10-continued

Seed oil percentage in seed with different hypodermis pigmentation.

| Progeny | Hypodermis pigmentation | Oil %† | LSD‡ |
|---------|-------------------------|--------|------|

‡LSD (0.05) = 0.70. Different letters indicate that means are statistically different. F-test were significant at the 0.001 level of probability for both progenies.

Seed with unpigmented hypodermis (HA89 type) had ten percent (3–4 percentage points) higher seed oil percentage than white pigmented hypodermis seed (ZENB8 type) in both types of progeny. In $F_3$ families segregating for hypodermis pigmentation the mean oil percentage is closer to the white class than to the unpigmented one.

The Hyp locus is located in the same genomic region (linkage group G') where a QTL with a major effect for seed oil percentage has been located in this population (FIG. 4). Gene action at this region was dominance for low oil percentage. ZENB8 alleles contributed the low oil percentage. The higher oil percentage effect at this region was explained by the higher kernel (or lower hull) percentage effect of alleles coming from the line with higher seed oil and kernel percentages (HA89). But this similar map position explains the relation between seed hypodermis color and oil percentage in this population.

In summary, a major dominant factor (Hyp) controlling hypodermis pigmentation was identified in linkage group G'. Phenotypic studies showed that seeds with white hypodermis color had lower oil percentage than those with unpigmented hypodermis. This Hyp factor was located in the same genomic region as one QTL with major effect controlling seed oil percentage. This is probably responsible for the relation between hypodermis pigmentation and oil percentage in this population. Thus, this invention provides a method for selectively breeding for the production of an improved sunflower with high oil percentage with or without the RFLP data. Because of the close association of the hypodermis pigmentation chromosomal region with the linkage group G a crude but effective visual screening of the pigmentation of the seeds of sunflower populations can permit selection for further breeding of those plants which carry the higher oil percentage trait. This can be confirmed by RFLP data or by processing the seed and determining oil levels.

We claim:

1. A sunflower breeding method employing a sunflower RFLP map for producing progeny sunflowers having improved seed oil content from a first parent line having high yield traits and low seed oil traits and a second parent line having a higher seed oil trait, said method comprising the steps of:

(a) crossing said first parent line with said second parent line and forming a plant population;

(b) gathering RFLP data on said plant population and selecting plants from said population which have linkage blocks which indicate the higher seed oil trait of the second parent;

(c) breeding said selected plants wherein a high seed oil content trait is evidenced in said progeny.

2. A method of identifying chromosomal regions of the sunflower associated with selected traits comprising the steps of:

(a) employing RFLP probes to locate chromosomal regions of the sunflower;

(b) mapping said RFLP probes on a RFLP map whereby selected traits can be identified and located.

3. A method of breeding for sunflower progeny having improved seed oil traits beyond the seed oil trait evidenced by at least one parent comprising the steps of:

(a) crossing a first sunflower having an unpigmented hypodermis contributing to a first seed color associated with high seed oil trait with a second sunflower having a pigmented hypodermis contributing to a second seed color and forming a plant population;

(b) selecting plants having an unpigmented hypodermis from said plant population whereby further breeding of said selected plants produces progeny characterized by said unpigmented hypodermis and said associated high oil trait.

* * * * *